US00RE36460E

United States Patent [19]

Klatz et al.

[11] E Patent Number: Re. 36,460

[45] Reissued Date of Patent: Dec. 21, 1999

[54] METHOD OF PROVIDING CIRCULATION VIA LUNG EXPANSION AND DEFLATION

[75] Inventors: Ronald M. Klatz; Robert M. Goldman, both of Chicago, Ill.; Michael G. Federowicz, Riverside, Calif.

[73] Assignee: Life Science Holdings, Inc., Chicago, Ill.

[21] Appl. No.: 09/070,795

[22] Filed: May 1, 1998

Related U.S. Patent Documents

Reissue of:

[64] Patent No.: 5,653,685
Issued: Aug. 5, 1997
Appl. No.: 08/412,135
Filed: Mar. 28, 1995

U.S. Applications:

[63] Continuation-in-part of application No. 08/383,240, Feb. 3, 1995, Pat. No. 5,584,804, which is a continuation-in-part of application No. 08/069,916, Jun. 1, 1993, Pat. No. 5,395,314, which is a continuation-in-part of application No. 07/886,041, May 19, 1992, Pat. No. 5,234,405, which is a division of application No. 07/595,387, Oct. 10, 1990, Pat. No. 5,149,321.

[51] Int. Cl.[6] ..... A61M 37/00

[52] U.S. Cl. ..... 604/26; 128/898; 128/201.21; 604/24; 604/56

[58] Field of Search ..... 604/27–28, 54, 604/49, 23–26, 56; 128/201.21, 200.24, 204.15, 898

[56] References Cited

U.S. PATENT DOCUMENTS

| | | |
|---|---|---|
| 4,173,654 | 11/1979 | Scherer . |
| 4,232,665 | 11/1980 | Vaseen . |
| 4,657,532 | 4/1987 | Osterholm . |
| 5,084,011 | 1/1992 | Grady . |
| 5,085,630 | 2/1992 | Osterholm . |
| 5,158,536 | 10/1992 | Sekins et al. . |
| 5,200,176 | 4/1993 | Wong . |
| 5,238,683 | 8/1993 | Crystal . |
| 5,272,252 | 12/1993 | McLean . |
| 5,335,650 | 8/1994 | Shaffer et al. . |
| 5,403,834 | 4/1995 | Malfroy-Camine . |

OTHER PUBLICATIONS

"Attempts at liquid Breathing, Technologies May Save Preemise, Treat Illnesses", by Tim Friend, *USA Today,* May 31, 1994, p. 05D.

"Partial Liquid Ventilation Promising in Preemies With Severe RDS," by Calvin Pierce, Nov. 1994.

"Cardiac Output During Liquid (Perfluorocarbon) Breathing in Newborn Piglets", Scott E. Curtis, MD, Bradley P. Fuhrman, MD, Donna F. Howland, BS, Maria DeFrancisis, BS Etsuro K. Motoyama, MD, *Official Journal of the Society of Critical Care Medicine,* vol. 19, No. 2, Feb. 1991, pp. 225–230.

"The Effects of Liquid Ventilation of Cardiopulmonary Function in Preterm Lambs", by Thomas H. Shaffer, Patricia R. Douglas, Corinne A. Lowe, and Vinod K. Bhutani, *Pediatric Research—An International Journal of Clinical, Laboratory and Developmental Investigation,* vol. 17, No. 4, Apr. 1983, pp. 303–306.

(List continued on next page.)

*Primary Examiner*—Corrine McDermott
*Attorney, Agent, or Firm*—Oliff & Berridge, PLC

[57] ABSTRACT

The invention discloses a method for providing circulation, usually when it has substantially decreased or ceased, such as during cardiac arrest. The method includes the steps of intubating the airway of a patient, to provide access to the lungs. The air and other material in the lungs is then evacuated. A liquid breathing solution is then infused into the lungs, expanding the lungs such that the lungs compress the heart and great vessels, to generate cardiac outflow and ultimately circulation. A device that performs this method is also disclosed.

22 Claims, 4 Drawing Sheets

OTHER PUBLICATIONS

"Instrumentation For Measuring Cardiac Output by Direct Fick Method During Liquid Ventilation", by E.M. Siveri, G.D. Moskowitz and T.H. Shaffer, *Undersea Biomedical Research,* vol. 8, No. 2, Jun. 1981, pp. 75–83.

"Decompression Incidence in Air—And Liquid Breathing Hamsters", by P.R. Lynch, J.S. Wilson, T.H. Shaffer, and N. Cohen, *Undersea Biomedical Research,* vol. 10, No. 1, Mar. 1983, pp. 1–10.

"Liquid Ventilation in Dogs: An Apparatus for Normobaric and Hyperbaric Studies", by D. J. Harris, R.R. Coggin, J. Roby, M. Frrxot, H. Turner, and P.B. Bennett, *Journal of Applied Physiology,* vol. 54, No. 4, ISSN 0161–7588, Apr. 1983, pp. 1141–1148.

"Easier Breathing in RDS", *Medical Tribune,* Jan. 11, 1990.

Program and Abstracts for the 26$^{th}$ Educational and Scientific Symposium, Official Journal of the Society of Critical Care Mecicine, vol. 25/No. 1 (Suppl.) Jan. 1997.

METHOD OF PROVIDING CIRCULATION VIA LUNG EXPANSION AND DEFLATION

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation in part of application Ser. No. 08/383,240, filed Feb. 3, 1995, now U.S. Pat. No. 5,584,804, which is a continuation in part of application Ser. No. 08/069,916, filed Jun. 1, 1993, now U.S. Pat. No. 5,395,314, which is a continuation in part of application Ser. No. 07/886,041, filed May 19, 1992, now U.S. Pat. No. 5,234,405, which is a divisional of application Ser. No. 07/595,387, filed Oct. 10, 1990, now U.S. Pat. No. 5,149, 321.

FIELD OF THE INVENTION

This invention relates to an apparatus and method for treating patients suffering from trauma, i.e., cardiac arrest. More particularly, the present invention discloses an apparatus and method for providing circulation for resuscitating the heart. The method involves perfusing a liquid breathing solution including substances such as artificial blood components into the respiratory tract under positive and negative pressure, for the purpose of creating circulation of blood through the circulatory system.

BACKGROUND OF THE INVENTION

During cardiac arrest, the heart ceases to pump blood. Subsequently, there is no circulation, and the brain fails to receive freshly oxygenated blood. Without a steady supply of oxygenated blood, the brain will cease to function.

Current resuscitation techniques for cardiac arrest result in low patient survival rates. In hospitals and clinics with advanced cardiopulmonary resuscitation (CPR) and life support systems, the survival rate is normally around 14%. Outside of hospital settings, the survival rate is about 5%.

Among cardiac arrest victims overall, less than 10% survive neurologically intact and without significant brain damage. The other approximately 90% either die or sustain some neurologic injury from ischemia, (i.e., lack of blood flow to the brain), or anoxia (i.e., lack of oxygen to the brain). Such frequency of neurologic injury occurs because after cardiac arrest, basic cardiopulmonary resuscitation and advanced life support techniques, such as CPR, closed heart cardiac chest massage, and electroshock treatments, typically require fifteen to twenty minutes to regain circulation from a failed heart. With conventional resuscitation methods, irreversible neurologic damage begins soon after circulation stops. Therefore, it is imperative to restart the heat as soon as possible.

SUMMARY OF THE INVENTION

The present invention improves on the prior art by providing a method for treating cardiac arrest, where circulation is resumed or enhanced. The method includes the initial steps of intubating the airway of a patient, to provide access to the lungs, and evacuating air and other material in the lungs. A liquid breathing solution (hereinafter "solution") is then infused into the lungs (via the intubation), expanding the lungs such that the lungs compress the heart and great vessels (aorta, aortic arch, vena cavx, pulmonary artery, pulmonary vein, subclavian artery, subclavian vein), to create cardiac outflow. In a subsequent step, some or substantially all of the liquid breathing solution in the lungs may be evacuated therefrom. This evacuation step allows the heart and great vessels to expand, thereby increasing in volume. Upon the completion of the evacuation step, additional solution may be infused into the lungs such that they again expand, to compress the heart and great vessels. These solution infusion and solution evacuation steps form a cycle that can be repeated for as long as desired.

The present invention includes a device for evacuating the lungs of air and other material, delivering the aforementioned liquid breathing solution to the lungs, and evacuating the aforementioned liquid breathing solution from the lungs. The device includes a reservoir for holding liquid breathing solution, which communicates with an oxygen tank, a heat exchanger and a valve controlled pump. The device also includes a defoaming/filtration unit, along a separate line, whose entry is controlled by a valve, for treating spent solution, prior to its reentry into the pump. The pump is capable of pumping in the reverse direction, to create suction for evacuating air and other material from the lungs, as well as evacuating spent liquid breathing solution, drawing it through the defoaming unit into the pump, and returning the treated (defoamed and/or filtered) solution to the reservoir (where it may be replenished or reoxygenated). The pump also pumps in the forward direction, to move solution from the reservoir out of the device, where it is infused (pumped) into the lungs of the patient. The forward pumping also moves waste material out of the device through a waste conduit. The oxygen tank upon activation, releases oxygen into the reservoir, oxygenating the liquid breathing solution therein, and depending on the pressure, assists the pump to move the solution out of the device. The movements of the pump and valve are controlled by a logic control unit.

BRIEF DESCRIPTION OF THE DRAWINGS

For a more complete understanding of the invention, reference should be made to the drawings wherein.

DETAILED DESCRIPTION OF THE DRAWINGS

Figure 1:
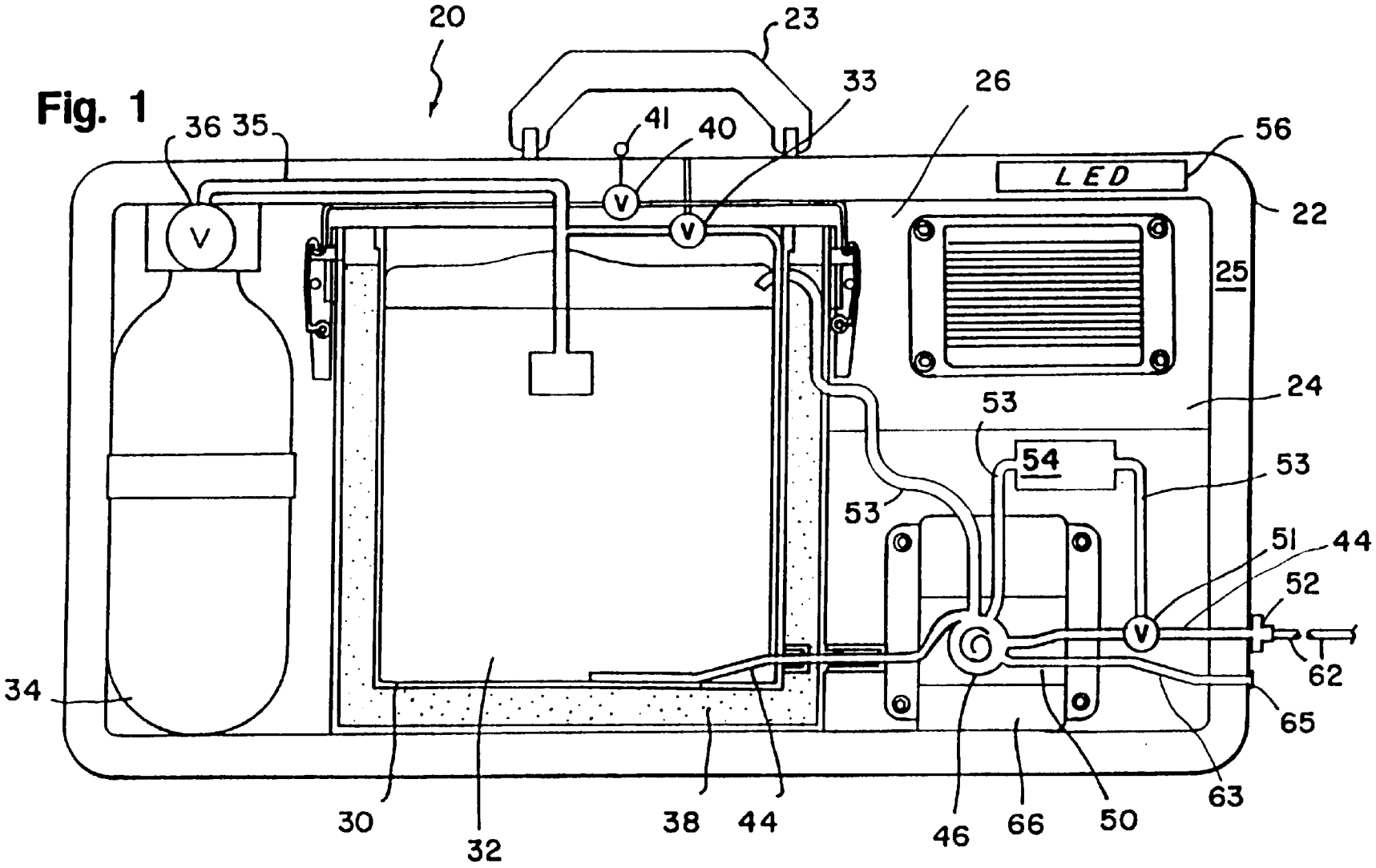
FIG. 1 is a front view of a first device used in performing the invention illustrating the internal components.
Figure 2:
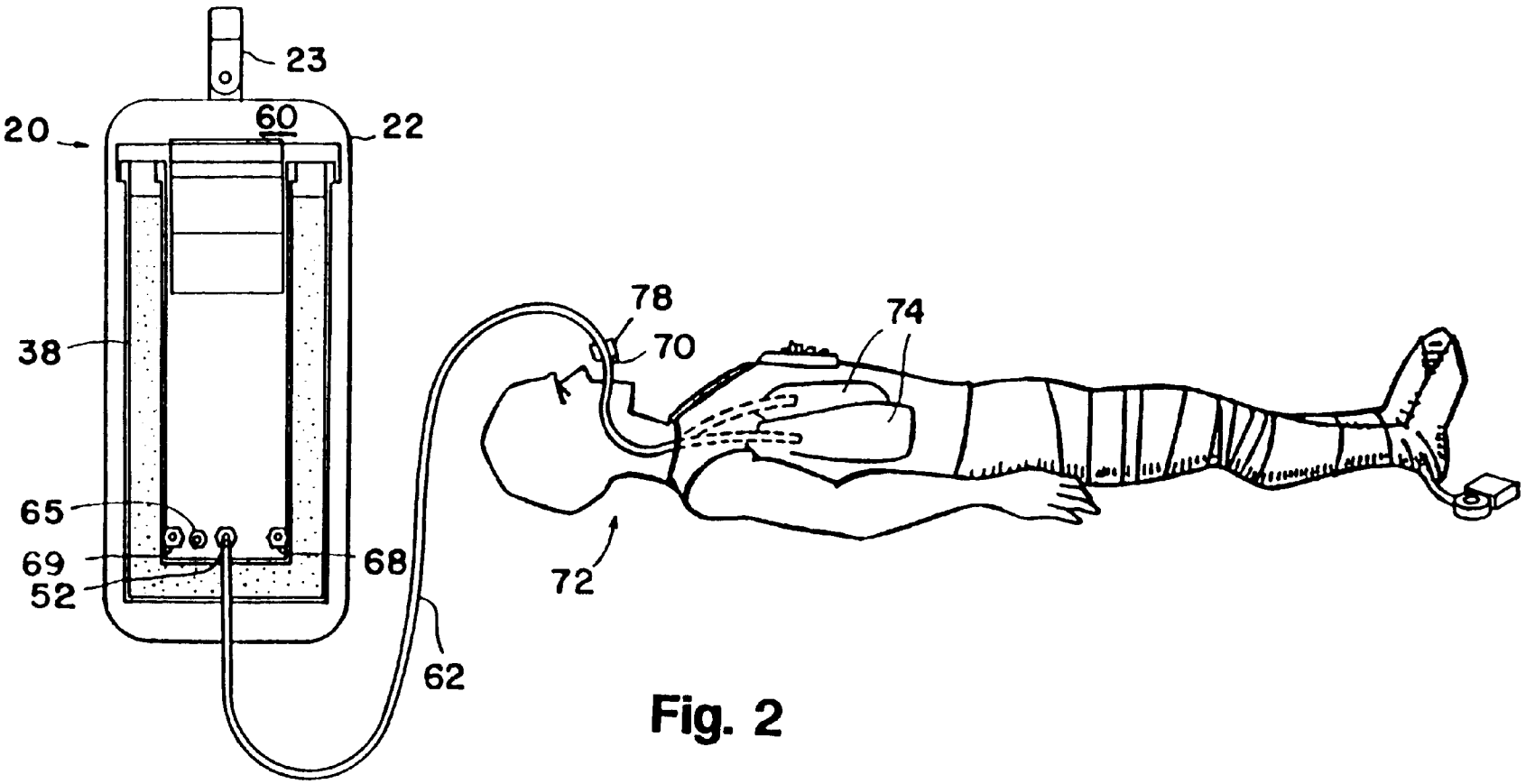
FIG. 2 is a side view of the first device of FIG. 1 in use to treat a patient.

Referring to FIGS. 1 and 2, the device 20 of the invention is semi-automatic. The device 20 includes an outer casing 22 with a handle 23 and a window 24. The window 24 is located within a first side 25 which has a greater width than length. The casing 22 includes an inner chamber 26. This inner chamber 26 contains components which include a reservoir 30, an oxygen tank 34, a heat exchanger 38, a pump 46, a logic control unit 50, and a power source 54.

The reservoir 30 holds the liquid breathing solution (hereinafter "solution"). The liquid breathing solution of this invention is a fluid mixture of various components and is packaged in premixed, premeasured canisters, for a single immediate use. These canisters can be replenished (refilled) and exchanged for continued application. The specific components are discussed below in accordance with the methods of the invention. Preferably, this reservoir 30 is adapted to hold up to ten liters of fluid contained within replaceable canisters 32. The preferred canisters are clear plastic bags, such that fluid depletion in the reservoir 30 can be viewed through the window 24. However, these canisters can be rigid containers, made of opaque materials, such as plastic, metal or the like. These canisters 32 may be equipped with pressure relief valves 33.

An oxygen tank 34, adjustable to various pressures, communicates with reservoir 30 through a first conduit 35. Oxygen tank 34 is sealed by a valve 36, which is opened once the device 20 is activated. Tank 34 is preferably a cylinder ten inches tall by four inches in diameter, containing oxygen pressurized to at least above atmospheric pressure. Tank 34 could also hold gases such as carbon dioxide, hydrogen or nitric oxide, and trace therapeutic gasses.

A heat exchanger 38, capable of controlling the fluid's temperature, surrounds reservoir 30. Preferably the heat exchanger cools by undergoing an internal endothermic reaction, once a charging valve 40 is opened when a charging handle 41 on the device is activated. The exchanger contains Ammonium Nitrate and water, which are initially separate. Upon activation, these chemicals contact each other, reacting endothermically, causing the heat exchanger to cool. Additionally, the heat exchanger's cooling can be accomplished by carbon dioxide (dry ice), freon (or other refrigerant gases) or a mechanical cooling device. Alternately, the heat exchanger 38 may contain chemicals that create an exothermic reaction for increasing the solution temperature above body temperature (as high as 125 degrees fahrenheit) and/or an electric heating element (powered by the logic control unit 50 and the energy source 66), or other mechanical heating element.

A second conduit 44 extends from the reservoir and communicates with a valve controlled pump 46 capable of pumping at various rates, directions (forward and reverse) and modes, in communication with a logic control unit 50. A filter (not shown) could be placed along the second conduit to remove unwanted contaminants.

The second conduit 44 extends through the pump 46 and logic control unit 50 through a two-way valve 51 and terminates in a side opening 52 on the device 20. This two-way valve 51 also controls flow of solution through a third conduit 53 for treatment in a defoaming and filtration unit 54 (hereinafter "defoaming unit") prior to reentry into the reservoir 30. Preferably, this side opening 52 is on the side 60 adjacent to the longitudinal side 25. Side opening 52 is capable of attaching to a tube 62, that connects to an endotracheal tube 70 in a patient 72 (the patient 72 having been intubated) at an adapter 78, such that solution can enter the patient's airway and ultimately the lungs 74, in accordance with the method of the invention.

The third conduit 53 extends from the two-way valve 51 to the valve controlled pump 46 and extends to the reservoir 30. The defoaming unit 54 is preferably along the third conduit 53, intermediate the two-way valve 51 and the valve controlled pump 46. Alternately, the defoaming unit 54 could be placed along the third conduit 53 intermediate the valve controlled pump 46 and the reservoir 30. The valve controlled pump 46 draws the solution that was treated in the defoaming unit 54, and pumps it into the reservoir 30, through the third conduit 53. The defoaming unit 54 includes a defoamer, a carbon dioxide scrubber and a filter(s). Suitable defoaming units include those commercially available models such as the ULTIPOR® blood filter EC3840 from Pall Biomedical Products Corporation, East Hills. N.Y. 11548, in combinations of one or more.

This valve controlled pump 46 may also control flow to a waste conduit 63 that allows waste (fluids, gases, solids, including solution, bodily fluids and tissue particulates, or other material) to leave the device 20. Specifically, the waste exits the device through a side waste opening 65.

The valve controlled pump 46 and the logic control unit 50 and two way valve 51 are powered by an energy source 66. However, the device is suitable for an electric adapter. A battery pack is the preferred energy source 66.

The logic control unit 50 includes (not shown) an oxygen pressure sensor, a fluid mass flow sensor, a fluid volume indicator and regulator, a fluid pressure indicator and regulator, a fluid temperature indicator and regulator, a fluid temperature indicator with feedback to a mass sensor, and a timing device for estimating the time the fluid in the reservoir will be depleted at a given mass flow. The logic control unit 50 includes a microprocessor for controlling the movements of the valve controlled pump 46 and the two-way valve 51. However, the logic control unit 50 may be manually overridden as the valve controlled pump 46 and two-way valve 51 may be controlled manually. Measurements from the logic control unit 50 are displayed on an LED or LCD digital display 56. Digital display 56 preferably shows the temperature and flow rate of the solution.

With respect to tube 62, high pressure respirator tubes, such as those typically used in high pressure respirators or ventilators or conventional heart-lung bypass pumps, are preferred. Additionally, it is preferred that the adjacent side 60 also contain openings for waste 65, for venting excess oxygen 68 and for oxygen intake 69. This oxygen intake can be from the atmosphere or from adjunct oxygen sources.

The device 20 is able to withdraw solution and waste from the patient by running the valve controlled pump 46 in reverse. When waste material is being removed, the two-way valve 51 opens the second conduit 44, such that solution flows directly to the valve controlled pump 46, where it pumps in the forward direction to move the waste material out of the device 20 through the waste conduit 63. When spent solution is returned to the device 20 for treatment, the two-way valve 51 closes the second conduit 44 and opens the third conduit 53, such that spent solution is treated in the defoaming unit 54, returned to the valve controlled pump 46, and pumped to the reservoir 30, through the third conduit 53.

Solution is infused into the lungs as the two-way valve 51 opens the second conduit 44, and closes the third conduit 53 (the valve controlled pump 46 is such that the third conduit 53 as well as the waste conduit 63 are closed). The oxygen tank valve 36 is opened and pressurized oxygen is released from the oxygen tank 34 into contact with the liquid breathing solution, thereby oxygenating it. The heat exchanger 38 is activated by releasing the charging valves 40. Once activated, the oxygenated solution in the reservoir 30 is cooled. This cooled solution moves through a second conduit 44, forced by sufficient pressure from the oxygen tanks 34 or drawn by sufficient pressure from the valve controlled pump 46 into the logic control unit 50. The pump 46 within this logic control unit 50 further moves the chilled oxygenated solution through this second conduit Solution then enters a tube 62, attached to an opening 52 in device 20 whereby it is delivered to the endotracheal tube 70 (as placed in a previously intubated or tracheotomized patient 72) and ultimately to the lungs 74.

Figure 3:
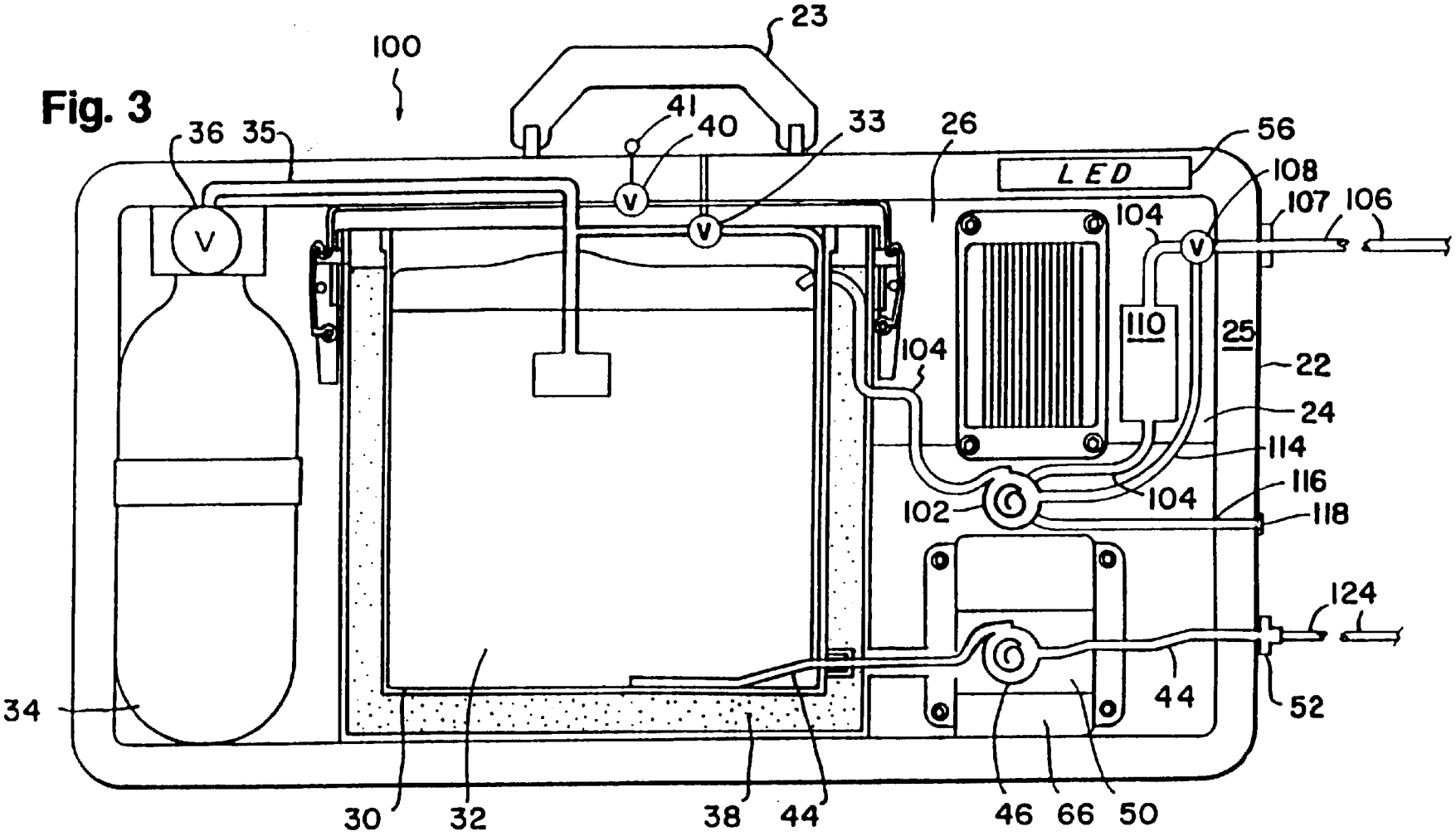
FIG. 3 is a front view of a second device used in performing the invention illustrating the internal components.
Figure 4:
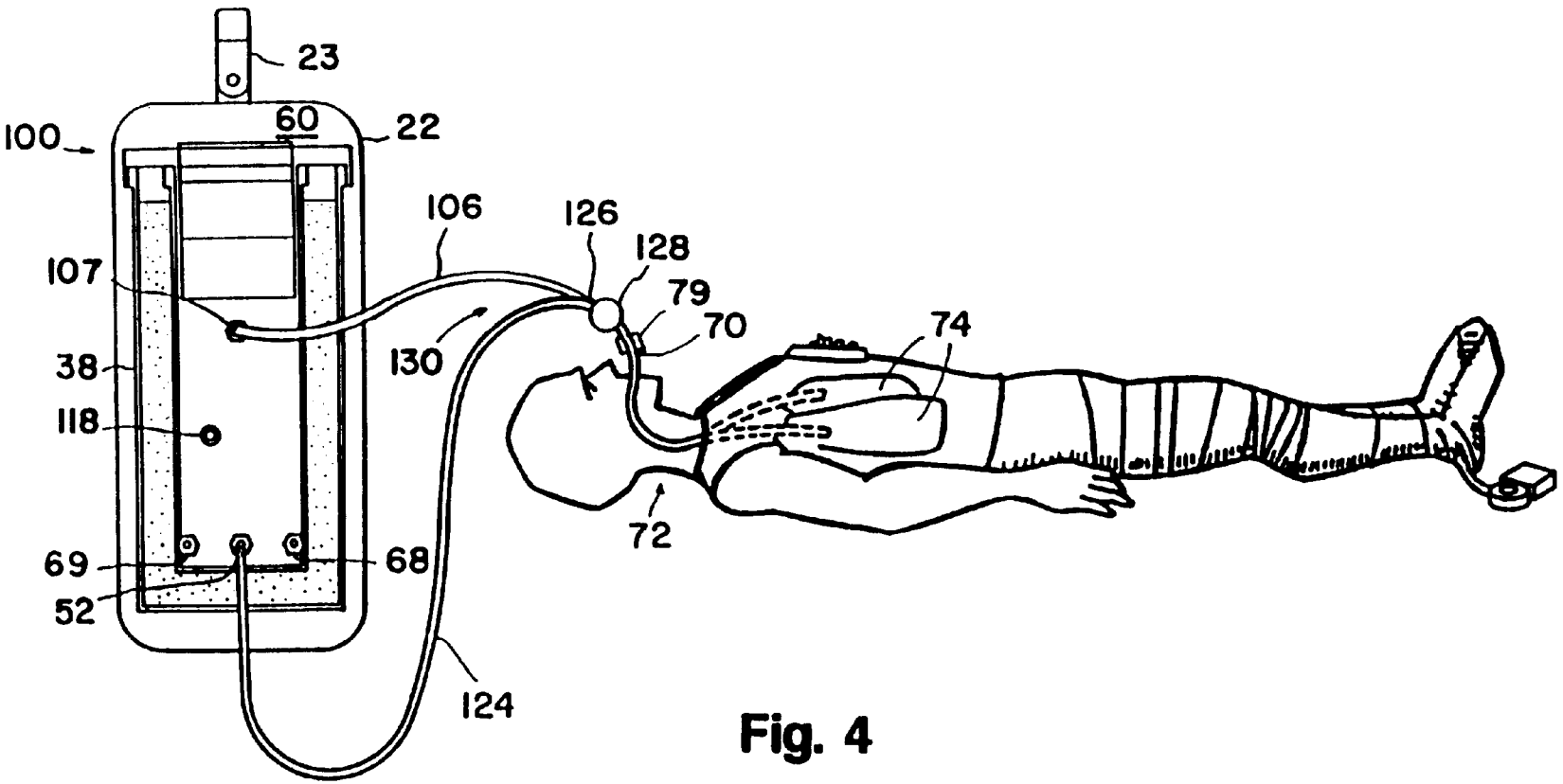
FIG. 4 is a side view of the second device of FIG. 3 in use to treat a patient.

FIGS. 3 and 4 show a second device 100 of the invention. The device 100 is similar to the first device 20 disclosed above (in FIGS. 1 and 2) except that this device 100 includes two pumps. The first valve controlled pump 46 is similar to that disclosed for the first device 20 above, and the second valve controlled pump 102 receives solution from a third conduit 104, that is fed solution through an inflow tube 106 (inflow of solution to the device 100) extending from the endotracheal tube 70 of the patient 72. The second valve controlled pump 102 is controlled by the logic control unit 50 and includes a separate series of inflow and outflow conduits.

This third conduit 104 originates at a side opening 107. (The first and second conduits 35, 44 are similar to that disclosed for the first device 20 above.) A two-way valve 108, controlled by the logic control unit 50 (similar to that disclosed for the first device 20 above), regulates solution flow to the third conduit 104. A defoaming unit 110 is positioned along this third conduit 104 prior to its entering the second valve controlled pump 102. The defoaming unit 110 may be any of those disclosed for use in the first device 20 (FIGS. 1 and 2 above). This third conduit 104 then exits the second valve controlled pump 102 and extends to the reservoir 30. The defoaming unit 110 may alternately be placed along this third conduit 104, intermediate the second valve controlled pump 102 and the reservoir 30, if desired.

A fourth conduit 114 extends from the two-way valve 108 to the second valve controlled pump 102. This fourth conduit 114 is designed to carry waste, and solution (if necessary) to the second valve controlled pump 102, where it is pumped through the waste conduit 116 and out of the device 100 through the side waste opening 118.

This device 100 forms a circular path for the solution, when it is used to perform the method of the invention. The logic control unit 50 is such that its microprocessor controls and coordinates the movements of the first and second valve controlled pumps 46, 102, (pumps and valves therein) and the two-way valve 108 to move solution into and out of the device 100 (and into and out of the patient 72) along a circular path. The positioning of the two-way valve 108 and second valve controlled pump 102 to move material or solution to the waste conduit 116 and out of the device when necessary, is also coordinated by the logic control unit 50. In this device 100, the side opening 107 receives the inflow tube 106. The side opening 107 communicates with the third conduit 104 that carries the solution through the two-way valve 108, opened to the flow path of the third conduit 104, such that the spent solution is treated in the defoaming unit 110, moved to the second valve controlled pump 102 and returned (by pumping) back to the reservoir 30.

Solution is infused into the lungs in a similar identical manner as described above for the first device 20. The solution reaches the patient 72 through an outflow tube 124 (outflow of solution from the device 100), that connects with the device 100 at the side opening 52, and that merges with the inflow tube 106 at a Y-shaped end 126, joining the endotracheal tube 72 at an adapter 78. A valve 128 may be placed at the Y-shaped end 126 for the purpose of increased control of directional flow of the solution such that there is minimal mixing of fresh (oxygenated) solution and spent solution in the inflow and outflow tubes 106, 124, and there is a minimization of dead space, such that the patient 72 will inhale a minimal amount of spent solution. The valve 128 is preferably a pressure controlled valve, responsive to pressure created by the directional flow of the solution. Alternately, the valve 128 may be a mechanical, manually controlled or automatically controlled valve, subject to the control of the microprocessor in the logic control unit 50 (as connected by wires to the logic control unit 50). The only structural difference is that the second conduit 44 in this second device 100 lacks the two-way valve 51 (FIG. 1).

Both devices 20, 100 are relatively small. They are portable, suitcase-like in appearance and suitable for field use, such as in ambulances, battlefields, athletic fields, aircraft, marine vehicles spacecraft, emergency treatment facilities, and the like. They are lightweight and can be carried directly to the patient. In one example of the device the outer casing measures forty inches by twenty four inches by twenty inches and weighs approximately fifty pounds. They are also suited for stationary, clinical use. Should a clinical device be desired, the devices could be made larger and modified accordingly for such use.

An alternative embodiment may have two or more reservoirs. These additional reservoir(s) can be formed by dividing the reservoir into multiple reservoirs or additional reserviors can be connected to the reservoir of the device with an adapter mechanism.

Still additional alternative embodiments may use preoxygenated solution in the reservoirs. Reservoirs containing preoxygenated fluid solution eliminate the need for oxygen tanks as these devices have sufficient power (enhanced electronics and powerful pumps), capable of moving the solution from the reservoir in the device to the lungs.

Another aspect of the invention comprises a method of treating cardiac arrest, suffered typically from suffocation, drowning, electrocution, losses of circulation, strokes, bodily injuries, toxic (carbon monoxide, cyanide, etc.) poisoning, and associated major trauma. Application of this method begins when a patient suffering from cardiac arrest is no longer breathing.

The initial step involves instrumentizing the trachea of the patient. This may be done by standard trachea intubation methods, preferably achieved with an endotracheal tube or other equivalent conduit. Alternately, an emergency tracheotomy (tracheostomy) may be performed in the neck in order to reach the trachea. This is typically achieved with a McSwain dart or other similar emergency type instruments.

Once the trachea has been intubated or otherwise instrumentized (such as by a tracheotomy), the tube 62 from the first device 20 or dual tube unit 130 from the second device 100 is connected to the endotracheal tube 70 by attachment with a adapter 78 or the like.

With the first device 20, the valve controlled pump 46 is now activated in reverse, such that the device automatically draws a vacuum to evacuate the desired amount of air (usually 4 to 8 liters-substantially the entire capacity of the lungs of an adult human) from the lungs. The material removed from the lungs during this evacuation step is brought into the device 20, with the valve in the pump 46 positioned such that this material enters the waste conduit 63 and leaves the device through the side waste opening 65.

With the second device 100, the second valve controlled pump 102 is initially activated with the two-way valve 108 opening the fourth conduit 114, to evacuate the lungs. Once sufficient pressure is drawn, the two-way valve 108 is closed as waste material is moved (by pumping) to the waste conduit 116, and leaves the device 100 through side opening 120.

Once the lungs are evacuated, in the first device 20 (FIGS. 1 and 2), the valve controlled pump 46 is switched to the forward direction. In the second device 100 (FIGS. 3 and 4), the first valve controlled pump 46 is now activated. In both devices 20, 100, the oxygen tank valves 36 are opened and pressurized oxygen is released from the oxygen tanks 34 into contact with the liquid breathing solution, thereby oxygenating it. The heat exchanger's 38 are activated by releasing the charging valves 40. Once activated, the oxygenated solutions in the reservoirs are cooled. These cooled liquid breathing solutions move through a second conduit 44, forced by sufficient pressure from the oxygen tanks 34 or drawn by sufficient pressure from the valve controlled pump 46 (first valve controlled pump 46 in the second device) into the logic control unit 50. The valve controlled pump 46 (first valve controlled pump 46 in the second device), within this logic control unit 50 further moves the chilled oxygenated solution through this second conduit. Solution then enters the respective tubes 62, (outflow tube) 124 attached to the side openings 52 in the devices 20, 100 whereby it is delivered to the endotracheal tube 70 (as placed in a previously intubated or tracheotomized patient 72) and ultimately to the lungs 74.

The solution is infused (pumped) to the lungs until it has replaced substantially all of the air spaces and/or residual volumes of gas therein, ultimately filling the lungs, such that they are expanded. This expansion compresses the heart and great vessels (aorta, aortic arch, vena cava, pulmonary artery, pulmonary vein, subclavian artery, subclavian vein) within the thoracic cavity, located between the lungs. Additionally, this expansion creates increased intrathoracic pressure (positive pressure) with sufficient force to compress the heart and great vessels, resulting in cardiac outflow sufficient to provide circulation in the body.

The solution is then evacuated from the lungs by suction created by the pumps (the second valve controlled pump 102 in the second device 100). Evacuating the lungs deflates them, reducing their volume, thereby decreasing pressure on the heart and great vessels. Additionally, this decrease in pressure creates decreased intrathoracic pressure (negative pressure) which allows the heart and great vessels to expand, resulting in the blood being drawn back toward the heart, creating venous blood flow.

These solution infusion and evacuation steps form a cycle that can be repeated as desired. This cycle is usually continued for as long as necessary to create circulation.

For example, the solution may be delivered in a series of pulses (pulsatile delivery). During pulsatile delivery, the valve controlled pumps on the devices are controlled to pump in both the forward and reverse directions. By pumping in both directions, the lungs may be evacuated and infused with fluid in a cyclic manner. Moreover, when solution is evacuated from the lungs, it can be replenished (reoxygenated) in the reservoir and returned to the lungs through the endotracheal tube (or equivalent instrumentation) through subsequent pumping in a later cycle.

The number of cycles for the pumps could be determined by the operator of the device. Optimal compression and expansion of the heart and great vessels is based upon the volume and pressure capacity of the lungs. Cardiac outflow, as a result of the compression and expansion on the heart and great vessels, can then be measured from biocompatible type sensors of blood pressure, capillary blood flow, tissue oxygen, tissue carbon dioxide, tissue pH, tissue lactic acid, blood oxygen, blood carbon dioxide, blood pH, blood lactic acid, EKG, EEG, ultrasound determination of cardiac wall measurement or heart chamber volume, pulse oximetry, pulse carbon dioxide measurement, or the like.

For example, the pumps (in the first device, the valve controlled pump, in the second device, the second pump) could first be brought into reverse, either automatically or manually. This reversal would involve a series of one or more pulses to extract a volume of air approximately equal to the airspace of the lungs. The pump could then deliver a solution in a present volume, at a present pressure, or at a present flow rate, in accordance with any one or all of these parameters, in a series of one or more pulses, to the lungs, whereby the lungs are maximally expanded. This typically requires approximately 4 to 8 liters for adult humans. Substantially the entire solution volume (the volume infused) could then be evacuated by the pumps (detailed above) operating in reverse. This solution is then treated in the defoaming units and returned to the reservoirs (where reoxygenation preferably occurs). Solution from the reservoir is then infused (pumped) into the lungs to repeat the cycle. This cycle can be continued for as long as desired, that is typically until the patient's circulation and breathing are restored.

An alternate method exists whereby once the lungs have initially been filled with solution (approximately 4 to 8 liters, as disclosed above) to a point where they are expanded (to compress the heart and great vessels), a smaller volume of solution (approximately 0.05 to 4.5 liters) is withdrawn and returned to the reservoir to be replenished (reoxygenated). Upon withdrawal of this smaller amount of solution, the lungs deflate (reduce in volume) slightly, such that the heart and great vessels are subject to less compression by the lungs, and thereby expand. Additional solution, in amounts approximately equal to that withdrawn form the lungs, would then be pumped into the lungs in pulses or a single stroke. This additional amount of solution would be infused (pumped) into the lungs at a sufficient pressure, to combine with and add to the volume of solution already in the lungs, whereby the lungs would again expand (increase in volume) to compress the heart and the great vessels.

The cooled solution also serves to cool the entire blood volume, as all blood circulates through the lungs by way of the great vessels of the heart (pulmonary artery and pulmonary vein) contacting the chilled solution which is pumped into the system by the device. The cooled blood circulates through the body, thus lowering the metabolism of the body, for the patient to survive neurologically intact. Since the cooled blood circulates to the brain and other organs, this method can be used for brain resuscitation and organ preservation in live patients. This method can also be used for organ preservation and total body cooling, as a method of achieving hypothermia in brain-dead patients and cadavers.

Once the lungs have been fully infused with solution, additional pumping of the heart, additional circulation of the solution, and additional fluid return of solution from the lungs (into the devices) may be desired. These additional actions may be achieved by external compression devices such as mast-trouser-like pneumatic or hydraulic compressive body garments (placeable any where along the body) or chest hydraulic, pneumatic or mechanical type percussion devices, or other equivalent devices. Additional circulation may be achieved by pneumatic or mechanical devices that impart rocking or thrusting motion to the body, thereby circulating and stirring the solution in the lungs.

The method of the invention may also be used to provide circulation in non-cardiac arrest situations. For example, it may be used to enhance circulation for patients with congestive heart failure. Also, it may be used to create circulation in patients suffering from cardiac tamponade, electromechanical dissociation, lethal cardiac arrythmia, or ineffective cardiac arrythmia. This method can also be used for drug delivery, as the solution infused into the lungs is absorbed into the lung tissues and other associated tissues by capillary absorption or diffusion across the membranes of the alveoli. These absorbed materials could then reach the bloodstream when the lungs oxygenate the blood during circulation.

For the methods of the invention, the liquid breathing solution is temperature controlled and delivered to the lungs, tissues and vasculature associated therewith, at temperatures at or below body temperature. Preferably, the solution is cooled below body temperature to approximately between forty and eighty degrees fahrenheit, but nay be cooled as low as −10 degrees fahrenheit. At temperatures below normal body temperature, the degenerative metabolism of the organ (s) is slowed as the subsequent free radical production ($O_2^-$ or other free radicals) decreases. This temperature-controlling step may alone allow up to an additional eight hours of organ viability, without neurologic damage. Alternately, the temperature controlling step may involve heating the solution to achieve warming or rewarning, to achieve hyperthermia or normothermia in the patient (or cadaver), for the purpose of achieving specific metabolic or physiologic effects and/or for the enhanced action and specific delivery of specific drug therapies in the patient. As stated previously, delivery of the chilled liquid breathing solution may be continuous or pulsatile, cyclic or non-cyclic, depending upon the type of pumps, logic control units and devices (disclosed above) in use for the specific method.

Additional cooling is achieved by applying external cooling means to the patient's head or chest area. The cooling means include a bonnet containing ice cubes synthetic cooling packets and the like. Alternately, cooling type wraps may be placed around the chest as well as cooling means applied the head, neck and back, such as those disclosed in U.S. Pat. No. 5,261,399 (Klatz et al.).

The solution is a mixture of various components suitable for maintaining breathing as well as keeping the lungs and associated tissues viable. Specifically, the solution is a fluid mixture that may include components such as oxygen carrying agents, antioxidants, barbiturates, carrier vehicles, physiologic buffers, nutrients, heavy metal scavengers, cytoprotective agents, ionotropic agents, electrolytes, metabolic mediators, anti-blood coagulating agents, neuroprotective agents, anesthetic agents, anti-inflamatories and other chemicals or combinations of chemicals. These other chemicals are generally known to those skilled in the art.

In the solution, oxygen carrying agents comprise about 0.00 to 99.99 percent by volume of this organ preservation solution. The preferred solution includes 10.00 to 99.00 percent by volume of oxygen carrying agents. Perfluorocarbons, hemoglobin based blood substitutes, or non-hemoglobin based blood substitutes are the preferred oxygen carrying agents, as they have an extremely high oxygen capacity. When delivered to the lungs, in this oxygenation step, these oxygen carrying agents may be supersaturated with oxygen, either having been oxygenated in the fluid reservoir or preoxygenated.

Antioxidants can be in the solution, in amounts up to 99.99 percent by volume. Preferably, the solution includes 0.001 to 30.000 percent by volume of antioxidants. These antioxidants are the preferred free radical scavengers. Once introduced into the organ(s), these antioxidants compete with organ tissue proteins as binding sites for the free radicals. Since a large portion of the free radials complex with antioxidants, a substantial amount of free radical damage is prevented since these same free radicals are inactivated by the antioxidants and do not bind to or form complexes with the proteins in the tissues of the lungs or other organs. The preferred antioxidants include Vitamin A (plus other carotenoids), Vitamin B, Vitamin C, Vitamin E, Selenium, Cysteine, BET, BHA, Hydergine, Glutathione (reduced) and the like.

Barbiturates may be included in the solution in amounts up to 20.00 percent. Preferred barbiturates include Thiopental, Secobarbital and Pentobarbital. Other commercially available barbiturates are also permissible.

The solution may include up to 99.00 percent by volume of components which act as carrier vehicles and diluents for the oxygen carrying agents (e.g., perfluorocarbons, hemoglobin based blood substitutes, and non-hemoglobin based blood substitutes) and antioxidants (if present in the solution). Dimethylsulfoxide (DMSO), Normosol® (Abbott Laboratories, North Chicago, Ill.), Mannitol, HES, Dextran 40, colloids, and crystalloids are the preferred carriers as they aid the above substances in traversing tissue cell membranes.

Additionally, the solution may contain physiologic buffers, such as HEPES (Monograph No. 4573, The Merk Index, Eleventh Edition) in amounts up to 50.00 percent by volume, to maintain pH.

Nutrients are also provided in this solution, up to 30.00 percent by volume. Glucose is one nutrient which is preferred.

The solution may also include up to 20.00 percent by volume heavy metal scavengers or chelating agents. These heavy metal scavengers or chelating agents would also serve to inhibit free radical damage. Desferoxamine is one preferred heavy metal chelator.

Cytoprotective agents such as Calcium Channel Blockers ($Ca^{++}$), Magnesium Sulfate, Potassium Chloride, Potassium sulfate, Calcium Chloride, THAM, and sodium phosphate dibasic, may also be present in this organ preservation solution in amounts up to 10.00 percent by volume. These cytoprotective agents, inhibit cell damage by stabilizing the cell membrane.

Ionotropic agents, such as epinephrine and dopamine, may be present in this solution up to 5.00 percent by volume.

Electrolytes, such as sodium chloride and magnesium chloride, may be present in this solution up to 10.00 percent by volume.

Additional metabolic mediators such as MK-801 and glutamate antagonists may also be in the solution up to 10.00 percent by volume.

The solution may contain up to 10.00 percent by volume of heparin or other suitable anti-blood coagulating agents to stop blood clotting which may occur due to lack of blood flow during cardiac arrest.

Neuroprotective agents may be in the solution in amounts up to 1.00 percent by volume. These neuroprotective agents may include acetyl-L-carnitine, ACEA 1021 (CoCensys, Inc.), CERESTAT® (Cambridge Neuroscience, Inc.), CPC 211, Freedox IV (tirlazed mesylate), Lidoflazine, Phenyotoin (dilantin), adenosine, gamma aminobutric acid, Lazeroids (The Upjohn Company, Kalamazoo. Mich.). GM1 Gangliosides, PGE, NMDA receptor blocker, PGBx, Fluarizine, Nicergoline, Nimodipine, Sabeluzole, Vincamine, Idebenome, Piracetum, Vinpocetin, and 11-Bromide-Vincamine.

Anesthetic Agents such as Phenobarbital (and its analogs), valium (and its analogs) and gamma hydroxy buterate (GEB) may be in the solution in amounts up to 5.00 percent by volume.

Finally, the solution may contain up to 5.00 percent by volume anti-inflamatories. These anti-inflamatories may include ibuprofen and acetylsalicylic acid.

From the foregoing description, it is clear that those skilled in the art could make changes in the described embodiments and methods of the invention without departing from the broad inventive concepts thereof. It is understood, therefore, that this invention is not limited to the particular embodiments disclosed, but it is intended to cover any modifications which are within the spirit and scope of the claims.

What is claimed is:

1. A method for providing circulation comprising:

establishing a pathway to the lungs of a patient suffering from impaired cardiac outflow by placement of a tube in an airway of the patient;

infusing a solution including oxygen carrying agents through the tube into the lungs of the patient to expand the lungs in order to compress the heart and great vessels a sufficient amount to increase cardiac outflow.

2. The method of claim 1, additionally comprising evacuating the lungs of air and other material prior to infusing the solution.

3. The method of claim 1, additionally comprising:

evacuating at least a portion of the solution from the lungs, through the tube, to deflate the lungs in order to expand the heart and great vessels; and again infusing an amount of solution through the tube into the lungs to again expand the lungs in order to compress the heart and great vessels a sufficient amount to increase cardiac outflow.

4. The method of claim 1, wherein the oxygen carrying agents include perfluorocarbons, hemoglobin based blood substitutes or non-hemoglobin based blood substitutes.

5. The method of claim 1, wherein the solution is infused into the lungs at at least normal body temperature of the patient.

6. The method of claim 1, wherein the patient suffers from cardiac arrest caused by at least one of suffocation, drowning, electrocution, loss of circulation, stroke, bodily injury, poisoning and major trauma.

7. The method of claim 1, wherein the patient suffers from cardiac arrest and application of the method begins when the patient is not breathing.

8. The method of claim 1, wherein the solution additionally includes free radical scavengers.

9. The method of claim 8, wherein the free radical scavengers include antioxidants.

10. The method of claim 1, wherein the solution is infused into the lungs at a temperature below normal body temperature of the patient.

11. The method of claim 1, wherein the solution is infused into the lungs at at least 80° F.

12. A method for providing circulation comprising:

providing an apparatus including a pathway, a solution holder that holds a solution including oxygen carrying agents, a pump configured to force solution from the solution holder through the pathway and a controller that controls infusion of the solution from the solution holder through the pathway into the lungs of a patient suffering from impaired cardiac outflow to expand the lungs of the patient in order to compress the heart and great vessels a sufficient amount to increase cardiac outflow;

using the apparatus to treat a patient suffering from impaired cardiac outflow by placing the pathway in an airway of the patient to establish a route to the lungs of the patient and infusing the solution from the solution holder through the pathway into the lungs of the patient to expand the lungs in order to compress the heart and great vessels a sufficient amount to increase cardiac outflow.

13. The method of claim 12, additionally comprising:

using the apparatus to evacuate the lungs of air and other material prior to infusing the solution.

14. The method of claim 12, additionally comprising:

using the apparatus to evacuate at least a portion of the solution from the lungs, through the pathway, to deflate the lungs in order to expand the heart and great vessels and again infusing an amount of solution through the tube into the lungs to again expand the lungs in order to compress the heart and great vessels a sufficient amount to increase cardiac outflow.

15. The method of claim 12, wherein the oxygen carrying agents include perfluorocarbons, hemoglobin based blood substitutes or non-hemoglobin based blood substitutes.

16. The method of claim 12, wherein the solution additionally includes free radical scavengers.

17. The method of claim 12, wherein the free radical scavengers include antioxidants.

18. The method of claim 12, wherein the solution is infused into the lungs at a temperature below normal body temperature of the patient.

19. The method of claim 12, wherein the solution is infused into the lungs at at least 80° F.

20. The method of claim 12, wherein the solution is infused into the lungs at at least normal body temperature of the patient.

21. The method of claim 12, wherein the patient suffers from cardiac arrest caused by at least one of suffocation, drowning, elcetrocution, loss of circulation, stroke, bodily injury, poisoning and major trauma.

22. The method of claim 12, wherein the patient suffers from cardiac arrest and application of the method begins when the patient is not breathing.

* * * * *